United States Patent [19]

Tanaka

[11] Patent Number: 5,348,704
[45] Date of Patent: Sep. 20, 1994

[54] APPARATUS AND METHOD FOR WASTE DISPOSAL

[75] Inventor: Damien R. Tanaka, Redding, Conn.
[73] Assignee: Medifor-X Company, Shelton, Conn.
[21] Appl. No.: 964,407
[22] Filed: Oct. 21, 1992
[51] Int. Cl.⁵ .......................... A61L 2/08; B30B 15/06
[52] U.S. Cl. ........................ 422/22; 422/300; 414/749; 100/229 A; 110/223
[58] Field of Search .............. 422/294, 22, 307–308; 110/223, 255; 414/749; 417/226, 227, 269, 521, 529; 100/229 A, 245

[56] References Cited

U.S. PATENT DOCUMENTS

| | | | |
|---|---|---|---|
| 2,107,507 | 2/1938 | Rose | 110/14 |
| 2,593,455 | 4/1952 | James | 23/252 |
| 2,731,208 | 1/1956 | Dodd | 241/41 |
| 2,898,198 | 8/1959 | Robedee | 23/252 |
| 3,541,949 | 11/1970 | Clar | 100/229 A |
| 3,765,346 | 10/1973 | Stockman | 110/8 R |
| 3,958,936 | 5/1976 | Knight, Jr. | 21/93 |
| 4,036,152 | 7/1977 | Bright | 110/223 X |
| 4,256,952 | 3/1981 | Thomas et al. | 422/307 X |
| 4,917,023 | 4/1990 | Jones | 110/230 |
| 4,988,262 | 1/1991 | Gines | 414/749 |
| 4,992,217 | 2/1991 | Spinello | 264/0.5 |
| 5,003,892 | 4/1991 | Bricken | 110/346 |
| 5,035,858 | 7/1991 | Held et al. | 422/21 |
| 5,078,924 | 1/1992 | Spinello | 422/294 X |
| 5,086,713 | 2/1992 | Dessí | 110/223 X |
| 5,106,594 | 4/1992 | Held et al. | 422/22 X |
| 5,178,828 | 1/1993 | Uesugi | 422/22 |

FOREIGN PATENT DOCUMENTS

| | | |
|---|---|---|
| 3505570C | 8/1986 | Fed. Rep. of Germany . |
| 3705364C | 5/1988 | Fed. Rep. of Germany . |
| 3701413A | 7/1988 | Fed. Rep. of Germany . |
| 90/11951 | 10/1990 | United Kingdom . |
| 2238535 | 5/1991 | United Kingdom ............ 422/22 |

OTHER PUBLICATIONS

Literature re Sutton Eco/Systems "MedAway-1" Regulated Waste Decontamination System, 4 pages, Apr., 1991.
Literature re the "MedAway-1" Waste Processor by MedMark International, 2 pages, Apr., 1991.

Primary Examiner—Robert J. Warden
Assistant Examiner—E. Leigh Dawson
Attorney, Agent, or Firm—Kramer, Brufsky & Cifelli

[57] ABSTRACT

An apparatus and method is provided for disposing of infectious waste. A decontamination chamber decontaminates the waste by dry heat sterilization, and a compactor reduces the volume of the waste subsequent to decontamination in the decontamination chamber. A robot assembly is mounted between the decontamination chamber and the compactor for automatically retrieving the waste from the decontamination chamber upon being decontaminated, and for transporting the waste to the compactor for volume reduction prior to disposal.

26 Claims, 7 Drawing Sheets

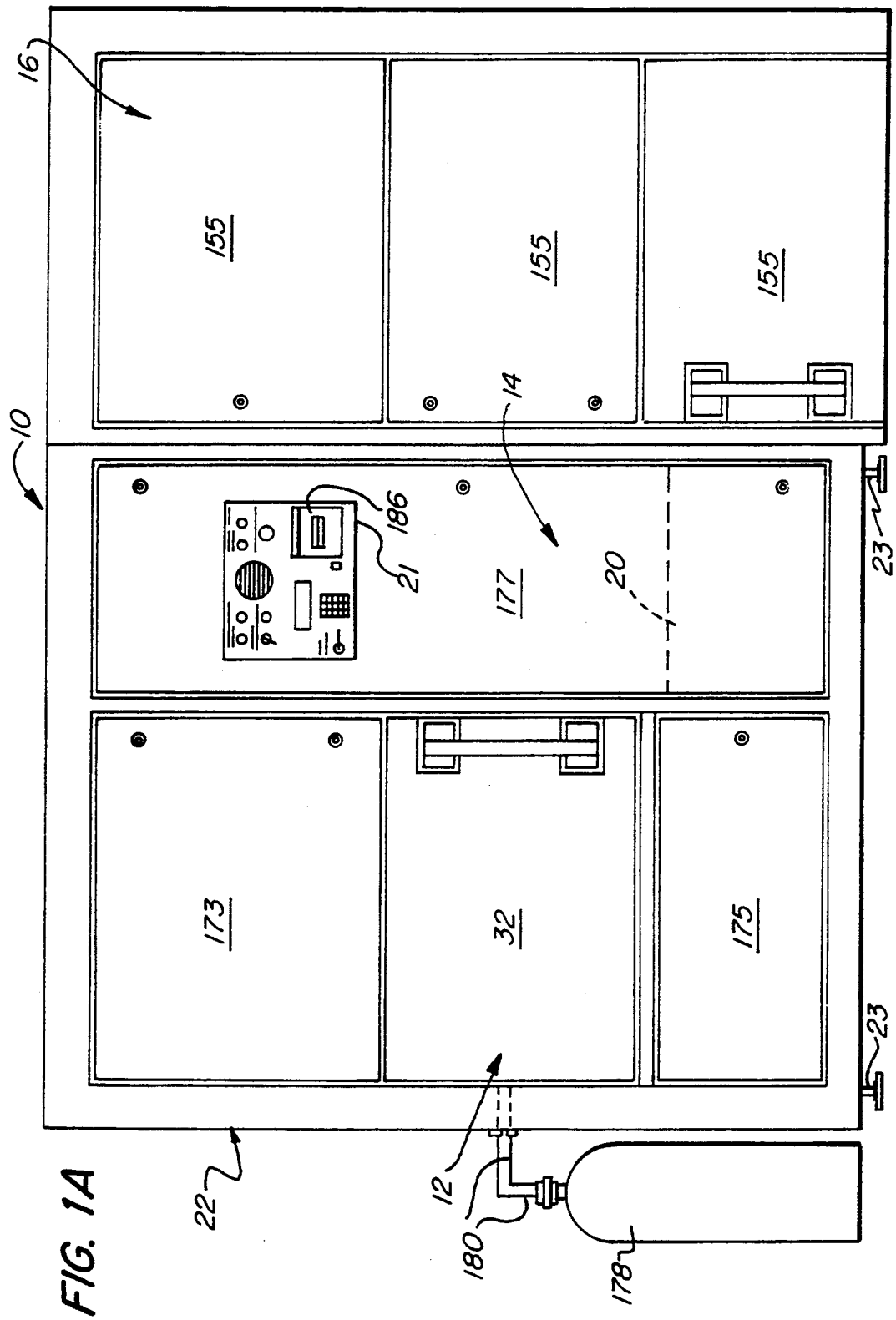

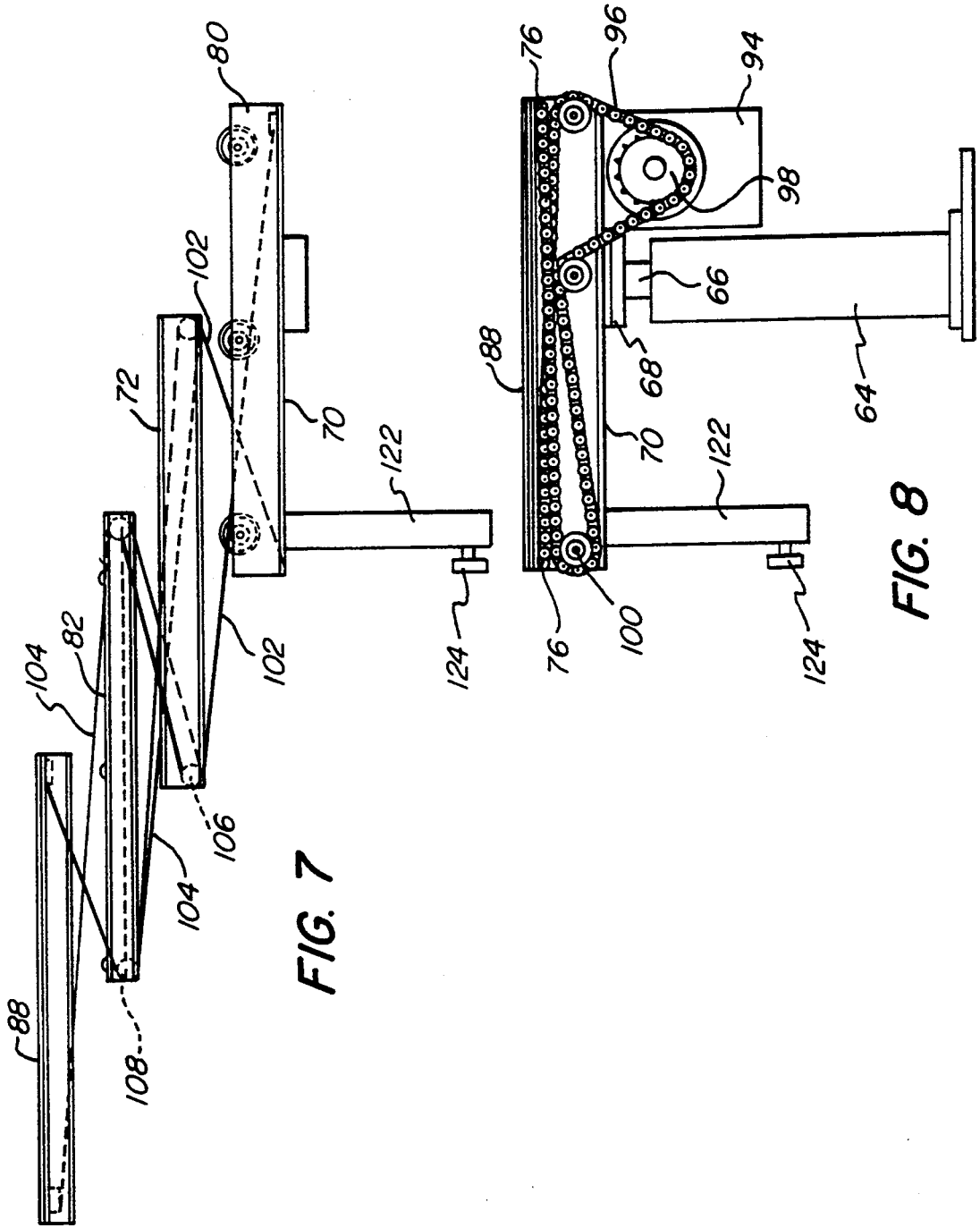

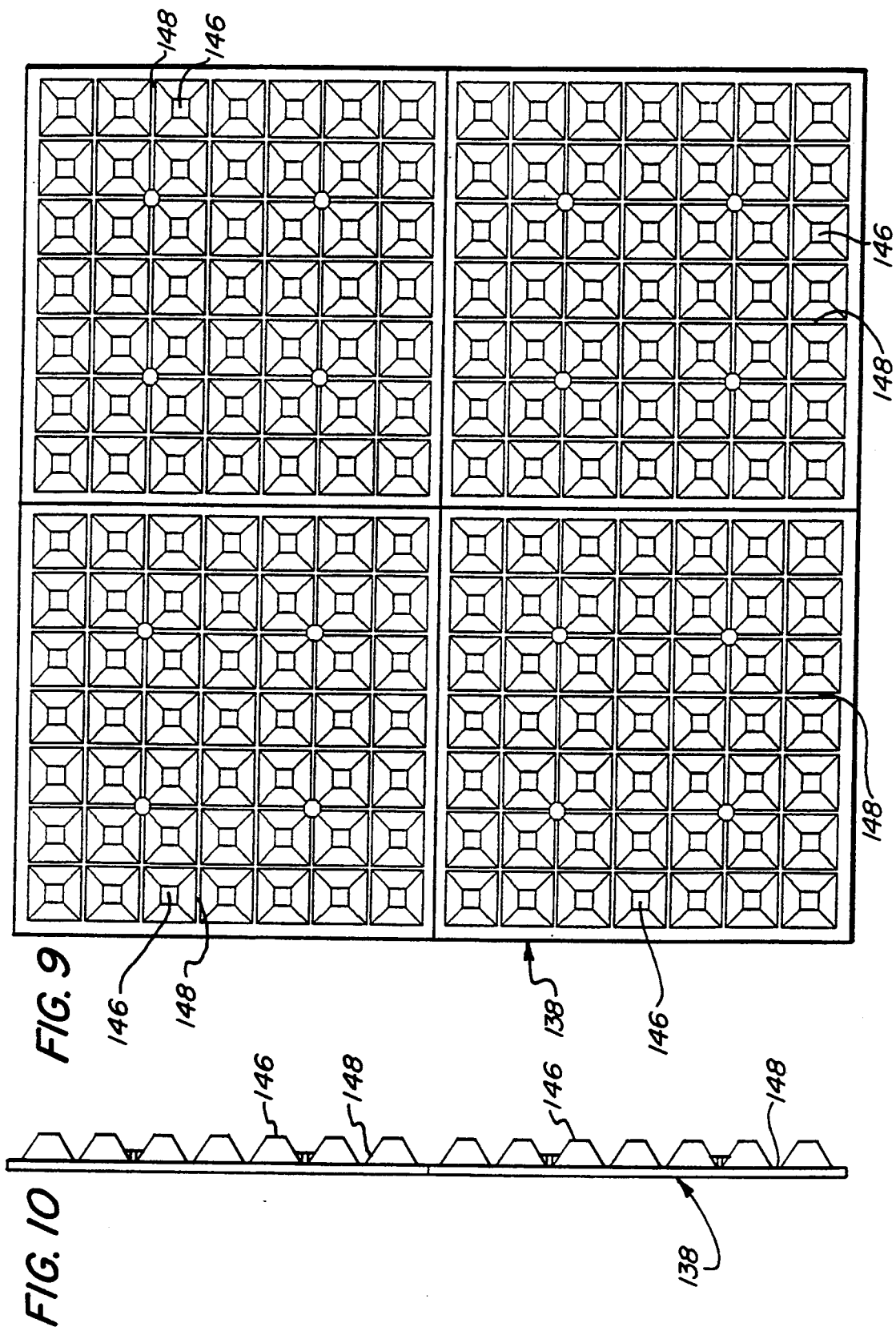

5,348,704

APPARATUS AND METHOD FOR WASTE DISPOSAL

FIELD OF THE INVENTION

The present invention relates to methods and apparatus for waste disposal, and more particularly, to methods and apparatus for treating regulated or infectious medical waste into a relatively safe, decontaminated state, and altering the appearance and reducing the volume of the treated waste for disposal as normal or unregulated waste.

BACKGROUND INFORMATION

Waste disposal is a particularly acute problem when the waste can cause infection, such as medical waste. Hospitals and other generators of medical waste typically employ at least one of three main methods of waste handling: 1) on-site incineration of the waste; 2) on-site steam auto-claving of the waste and later shipment to a landfill; and 3) no on-site processing before turning the waste over to a waste hauler.

Although on-site incineration decontaminates and effectively destroys the waste, the smoke stacks and emissions associated with such incinerators are particularly disfavored by the residents in and around hospital facilities. Moreover, unless such incinerators have sophisticated scrubber systems, they can emit harmful pollutants which can be equally as threatening to the public health as improper dumping of the infectious waste. Although steam auto-claving may be used to disinfect waste before further processing, it is typically an expensive and time-consuming process. In addition, such systems typically are not automated, thus posing hazards to the workers handling the waste, and possibly others.

Simply turning the infectious waste over to a waste hauler is particularly disadvantageous, since a spill or accident at any point in the handling of the waste can pose a serious health hazard to anyone in the vicinity of the spill or accident. It is always desirable to decontaminate the waste prior to handling to avoid any health hazards to anyone coming into contact with such waste.

What has been needed to date is an apparatus and method for decontaminating and disposing of infectious waste, in a manner which is safe for health care workers, waste handlers, and the public at large.

SUMMARY OF THE INVENTION

The present invention is directed to an apparatus for disposing of infectious waste. The apparatus comprises a decontamination chamber for decontaminating the waste, and a compactor for reducing the volume of the waste subsequent to decontamination. A robot assembly is mounted between the decontamination chamber and the compactor for automatically retrieving the waste from the decontamination chamber upon being decontaminated, and for transporting the waste to the compactor for volume reduction prior to disposal.

In one embodiment of the present invention, the decontamination chamber includes an access door for accessing the interior of the decontamination chamber, and a loading tray for holding the waste during decontamination. The loading tray is pivotally mounted within the decontamination chamber and coupled to the access door for swinging with the access door as it is opened and closed. The present invention preferably further comprises means for automatically locking the access door to prevent access to the decontamination chamber during decontamination.

One embodiment of the present invention further comprises a hot-air circulation system coupled to the decontamination chamber for circulating the air through the decontamination chamber and to facilitate heating the waste by convection. The hot-air circulation system preferably includes means for filtering the air within the decontamination chamber.

One embodiment of the present invention further comprises a cool-air circulation system for circulating air adjacent the robot assembly and through the compactor for cooling the decontaminated waste prior to compaction. The cool-air circulation system preferably includes a first filter for filtering particulates from the air, and a second filter for filtering gases and odors from the air prior to venting the air from the apparatus.

In one embodiment of the present invention, the robot assembly comprises a plate assembly including a plurality of plates, one mounted on top of the other, and means for driving at least one plate relative to the other to transport the waste between the decontamination chamber and the compactor. The robot assembly preferably further comprises a cylinder for driving at least one plate in the vertical direction for lifting the waste in the decontamination chamber and lowering the waste in the compactor.

In one embodiment of the present invention, the compactor comprises a compactor ram, a first drive cylinder including a first piston, and a second drive cylinder including a second piston coupled to the compactor ram. The first and second drive cylinders are oriented in a substantially parallel relationship relative to each other to drive the compactor ram. The compactor ram preferably defines a plurality of raised surface areas and a plurality of contiguous depressed surface areas surrounding the raised surface areas for facilitating compaction and altering the appearance of the waste upon being compacted.

The present invention is also directed to a method for disposing of waste comprising the steps of decontaminating the waste in a decontamination chamber; automatically retrieving the waste from the decontamination chamber upon being decontaminated with a robot assembly; transporting the decontaminated waste on the robot assembly to a compactor; automatically releasing the decontaminated waste with the robot assembly into the compactor; and compacting the decontaminated waste in the compactor.

In one embodiment of the present invention, the decontaminated waste is cooled prior to compaction. The decontamination is preferably carried out by dry heat sterilization including both radiation and convection heating components.

A significant advantage of the present invention is that it provides a system for automatically decontaminating highly infectious waste, and compacting and otherwise altering the appearance of the decontaminated waste for disposal. The waste is simply loaded into the decontamination chamber, and the system automatically processes the waste into a relatively safe and harmless state without any need for further operator handling or intervention. Moreover, the decontamination chamber preferably employs dry heat sterilization, which rapidly and thoroughly heats, and in turn renders the waste, such as polymeric waste, into a harmless decontaminated mass, which is then compacted for easy disposal. Accordingly, the smoke stacks and emissions of prior incinerator systems are entirely avoided, in a manner which is typically less expensive and less time consuming than prior steam auto-claving systems. Moreover, the decontaminated, compacted waste can simply be disposed of as normal or unregulated waste, thus avoiding the risks previously imposed upon waste haulers in transporting contaminated waste.

Other advantages of the apparatus and method of the present invention will become apparent in view of the following detailed description and accompanying drawings.

BRIEF DESCRIPTION OF THE DRAWINGS

FIG. 1A is a front plan view of an apparatus embodying the present invention.

FIG. 7 is an exploded plan view of the plates as shown in FIG. 5 illustrating the cable assembly connecting the plates together and for driving the plates relative to each other.

FIG. 8 is another side plan view of the robot assembly of the apparatus of FIGS. 1A and 1B illustrating the chain drive for driving the plates in the horizontal direction.

FIG. 9 is a plan view of the compacting surface of the compactor ram of the apparatus of FIGS. 1A and 1B.

FIG. 10 is a side plan view of the compacting surface of FIG. 9.

DETAILED DESCRIPTION

Figure 1B:
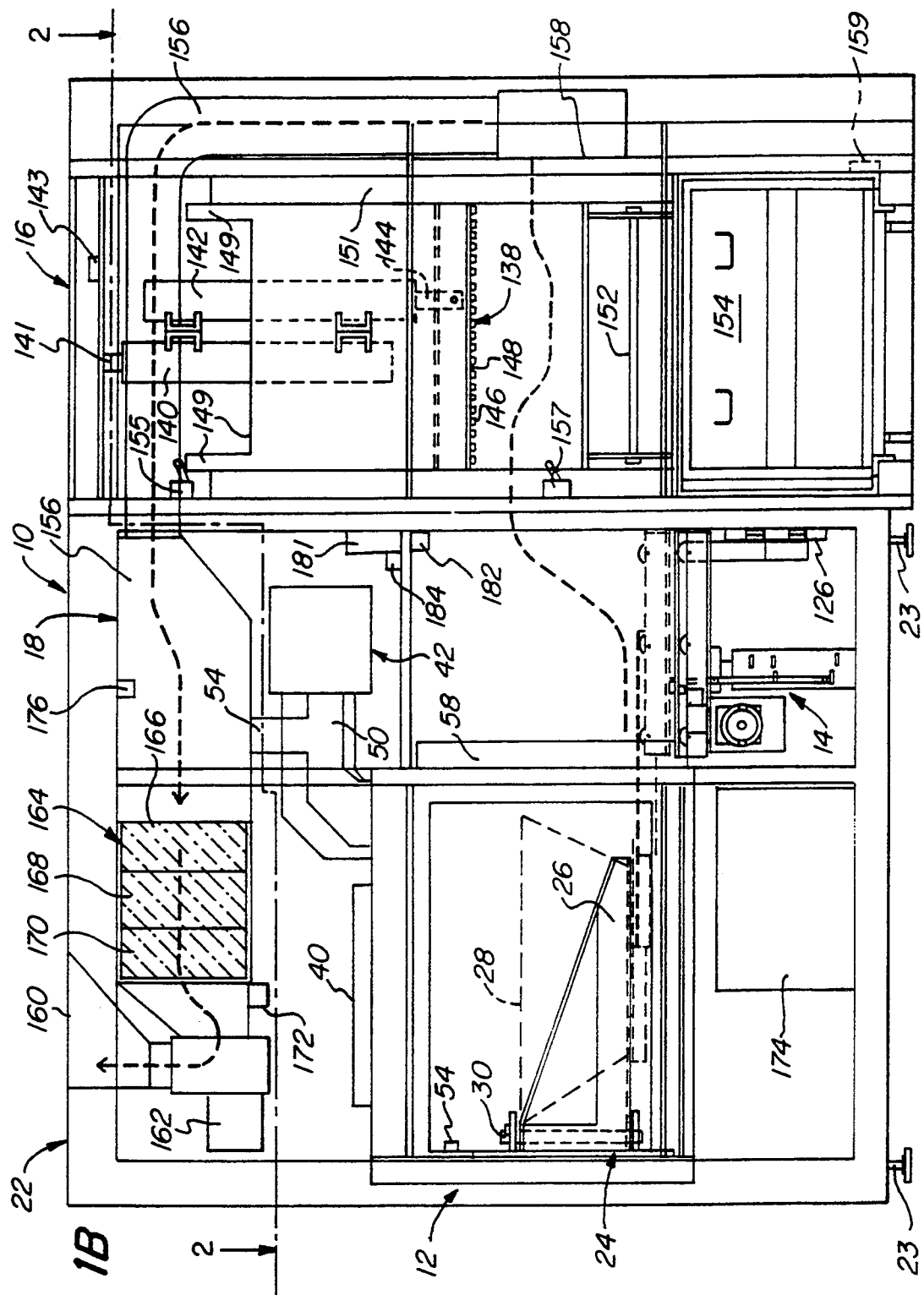
FIG. 1B is a schematic, cross-sectional view of the apparatus of FIG. 1A taken along the line 1—1 of FIG. 2.

In FIGS. 1A and 1B, an apparatus embodying the present invention for treating and disposing of waste is indicated generally by the reference numeral 10. As shown in FIG. 1B, the apparatus 10 includes a decontamination chamber 12 for thermally decontaminating the waste, a robot assembly 14 for transporting the decontaminated waste from the decontamination chamber 12, and a compactor 16 for receiving the decontaminated waste from the robot assembly 12 and compacting the waste in order to alter its appearance and reduce its volume for disposal. A cool-air circulation system 18 circulates relatively cool air through the space above the robot assembly 14 and through the compactor 16 (the direction of air flow is indicated by the dashed lines and arrows in FIG. 1B), to cool the decontaminated waste prior to being compressed in the compactor 16, and filters the air prior to venting the air into the atmosphere, as is described further below.

Figure 2:
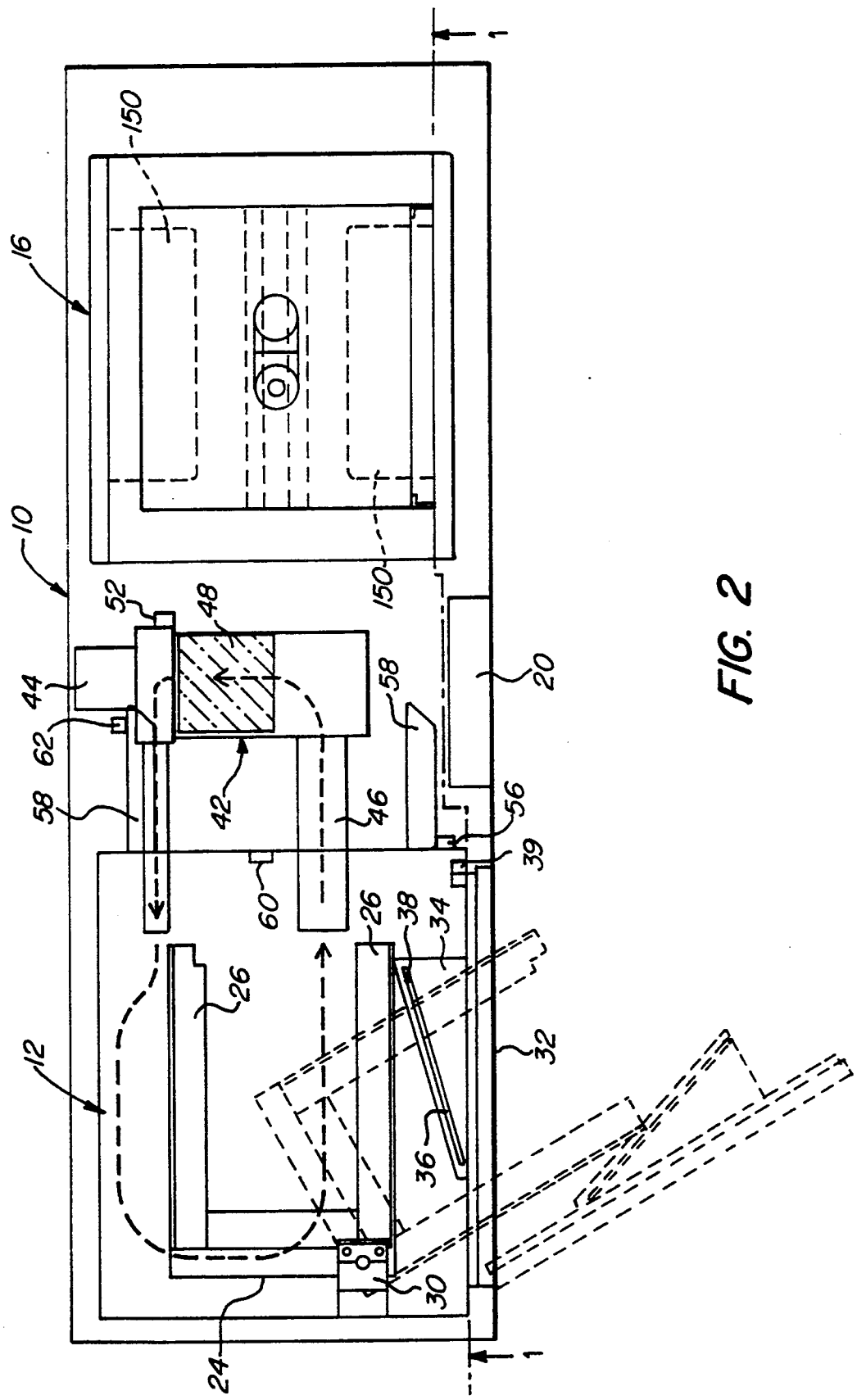
FIG. 2 is a cross-sectional view of the apparatus of FIG. 1B taken along the line 2—2 of FIG. 1B.

As shown in FIG. 2, a computer 20 is electrically coupled to each of the aforementioned components for automatically controlling the operation of the apparatus 10 and otherwise collecting and recording data pertaining to the operation of the apparatus. As shown in FIG. 1A, a control panel 21 is located on the front face of the apparatus 10 and is coupled to the computer 20 for controlling the operation of the apparatus. The apparatus 10 is contained within a frame and housing structure 22 which prevents access to the decontamination chamber 12, robot assembly 14, and compactor 16 during operation to avoid the possibility of injury to an operator, as is also described further below. The frame and housing structure 22 also includes levelers and castors 23 mounted on the base of the apparatus for facilitating movement and installation of the apparatus.

The decontamination chamber 12 comprises a loading tray 24 including a pair of loading arms 26 spaced apart from each other on either side of the loading tray for supporting a waste container 28, illustrated in dashed lines in FIG. 1B. The front side of the decontamination chamber 12 defines an access opening covered by a door 32, which is opened to gain access to the interior of the decontamination chamber 12 and to load the waste container 28 onto the loading tray 24. The waste container 28 is made of a corrugated cardboard material preferably coated with a high temperature reflective coating. The loading tray 24 is supported on one corner from the frame 22 by a hinge assembly 30 for pivoting the loading tray upon opening and closing the door 32, as indicated by dashed lines in FIG. 2. A position guide 34 is coupled to the inside of the door 32, and defines a guide slot 36 for receiving a guide member 38 coupled to the front loading arm 26 of the loading tray 24. The guide member 38 slides through the guide slot 36 as the door 32 is opened and closed, which in turn causes the loading tray 24 to swing with the door through the access opening, as indicated by the dashed lines in FIG. 2.

As the door 32 is opened, the loading tray 24 is automatically pivoted through the access opening and into a load position to receive and hold the waste container 28 in a horizontal position. Upon closing the door 32, the loading tray 24 is automatically pivoted into the closed position for decontaminating the waste so that the loading arms 26 are oriented generally parallel to the front face of the apparatus 10, as illustrated in FIG. 2. A solenoid-operated door lock 39 is coupled to the door 32 to automatically lock the door in the closed position. The door lock 39 is coupled to the computer 20, and when the decontamination chamber 12 is undergoing a decontamination cycle, the computer 20 maintains the door lock 39 in a locked position to prevent access to the interior of the decontamination chamber.

As shown in FIG. 1B, the decontamination chamber 12 also includes a far infrared heating panel 40 located on the top side of the chamber. The capacity of the heating panel 40 is selected depending upon the particular size and configuration of the decontamination chamber 12. In the embodiment of the present invention illustrated, a heating panel 40 having a capacity of approximately 6000 watts, satisfactorily operates the decontamination chamber within the range of approximately 180° C. to 250° C.

A hot-air recirculation and filtration system 42 is provided for circulating the air through the decontamination chamber 12 (the direction of air flow is indicated by the dashed lines and arrows in FIG. 2), and for filtering the air prior to introduction back into the decontamination chamber. A blower 44 draws the hot air from the decontamination chamber 12 through an exhaust duct 46, filters the hot air by passage through a filter 48, and introduces the hot air back into the decontamination chamber 12 through an entrance duct 50. The filter 48 is preferably a high temperature HEPA filter, which can remove particulates from the air, including smoke, having a particle size of less than 0.3 microns. A pressure gauge 52, such as magnahelic gauge, is coupled to the computer 20 for monitoring the pressure drop across the filter 48 to ensure that the filter is continuously monitored and replaced when necessary. The pressure gauge 52 transmits a signal to the computer 20 when the pressure drop across the filter 48 reaches a threshold value, and the computer 20 in turn initiates a time clock, so that upon expiration of a predetermined time period, a warning signal is generated to the operator to replace the filter 48. As shown in FIG. 1B, an exhaust bleed 54 is coupled between the entrance duct 50 and the cool air circulation system 18 to permit the hot air to bleed from the decontamination chamber 12 as necessary to compensate for thermal expansion.

A thermocouple 54 is mounted within the decontamination chamber 12 and coupled to the computer 20 to measure the temperature of the chamber, and to control the operation of the heating panel 40 so that the temperature of the chamber remains within approximately 1.5% of the set-point temperature. In the embodiment of the present invention illustrated, the set point temperature is within the range of approximately 180° to 250° C. for achieving a satisfactory decontamination rate.

One advantage of the apparatus of the present invention, is that the combination of the infrared heating panel 40 and the hot-air circulation and filtration system 42 provides a dry heat sterilization process, which thermally decontaminates the waste by primarily radiation and convection, along with conductive heating components. Thus, the waste is rapidly and thoroughly heated by three different heating components, and in turn thoroughly decontaminated in a relatively rapid period of time. In the embodiment of the present invention illustrated, thorough decontamination can be achieved within the range of approximately 15 to 45 minutes. Of course, the time period of the decontamination cycle can be adjusted by adjusting, for example, the capacity of the heating panel and/or the flow rate of air through the hot-air circulation system.

In prior waste disposal systems, employing only radiation and/or conductive heating components, it is more difficult to sufficiently heat and in turn decontaminate the waste at the center of the waste container. The addition of the convection heating component, as provided by the hot-air circulation system, to the radiation heating component, significantly facilitates that rapid and thorough heating, and in turn decontamination of the infectious waste. Polymeric medical materials are melted and transformed into a pool of liquid or gel-type mass within the bottom of the waste container 28. This is a particular advantage with polymeric containers and/or products containing sharps (such as needles and/or scalpels), since the sharps are deposited or contained within the melted polymeric mass, which is subsequently cooled to form a substantially solid polymeric mass enclosing the sharps, and thus preventing human contact with, and possible injury from the sharps.

The computer 20 is electrically coupled to a motor 56, which drives a pair of rear doors 58 enclosing the side of the decontamination chamber 12, as shown in FIG. 2. The rear doors 58 are normally closed during the decontamination cycle, as illustrated in FIG. 1B, but are driven open by the motor 56, as illustrated in FIG. 2, to permit the robot assembly 14 to transport the decontaminated waste from the decontamination chamber 12 to the compactor 16. Thus, once the decontamination cycle is completed, the computer 20 automatically controls the motor 56 to open the rear doors 58. A first position switch 60 transmits a signal to the computer 20 indicating that the rear doors 58 are closed, and a second position switch 62 transmits a signal to the computer 20 indicating that the rear doors are open. Once the computer 20 receives the signal from the second position switch 62 (indicating that the rear doors 58 are fully opened), it then controls the robot assembly 14 to remove the load of decontaminated waste from the decontamination chamber, as is described further below.

Figure 4:
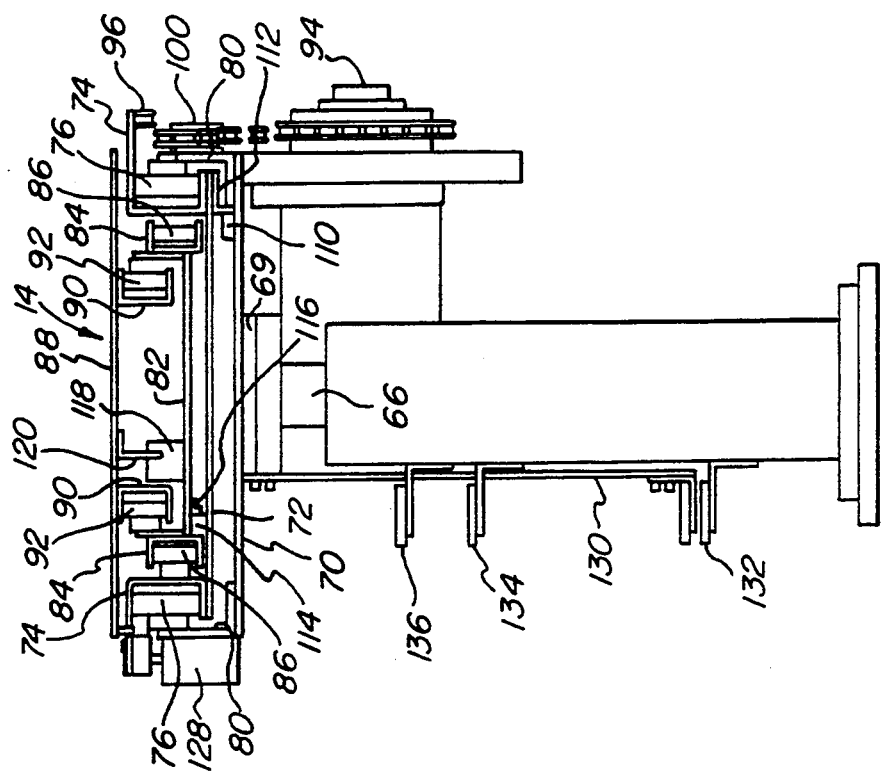
FIG. 4 is an end plan view of the robot assembly of FIG. 3.
Figure 3:
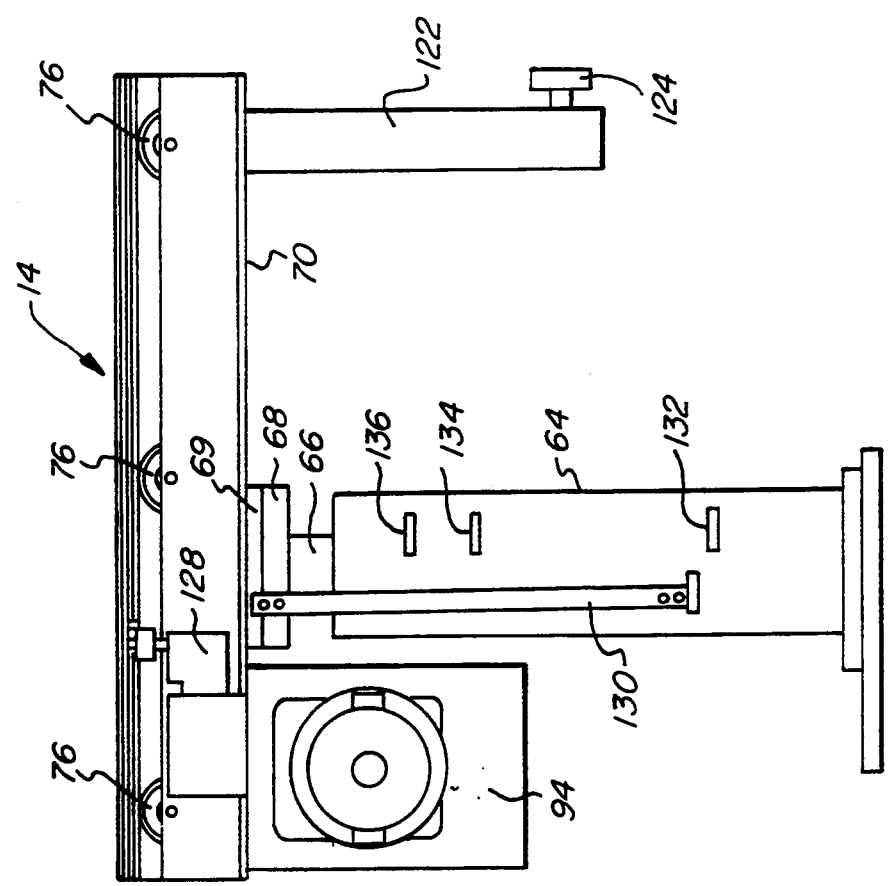
FIG. 3 is a front plan view of the robot assembly of the apparatus of FIGS. 1A and 1B.
Figure 5:
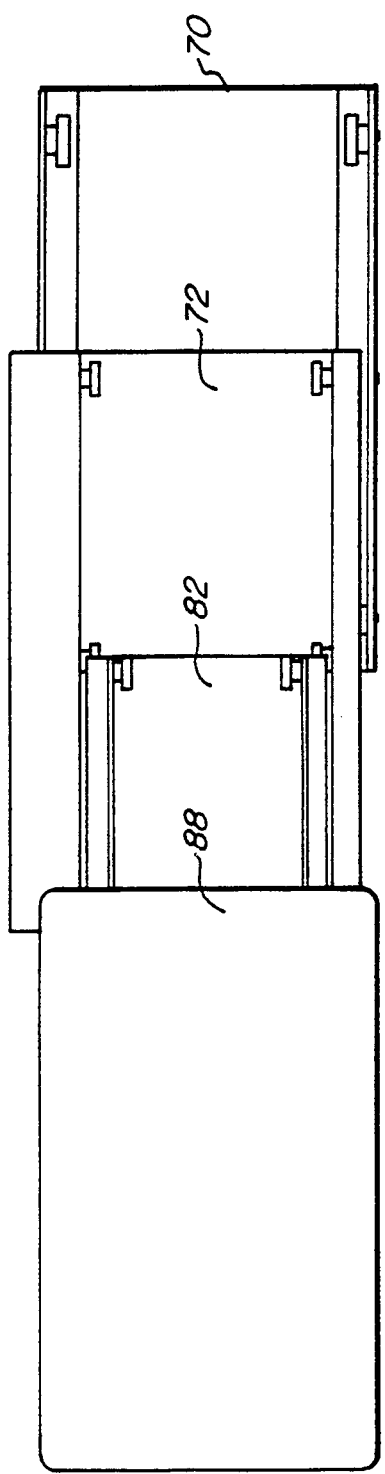
FIG. 5 is a top plan view of the plate assembly of the robot assembly of FIGS. 4 and 5 illustrating the plates in a fully extended position.
Figure 6:
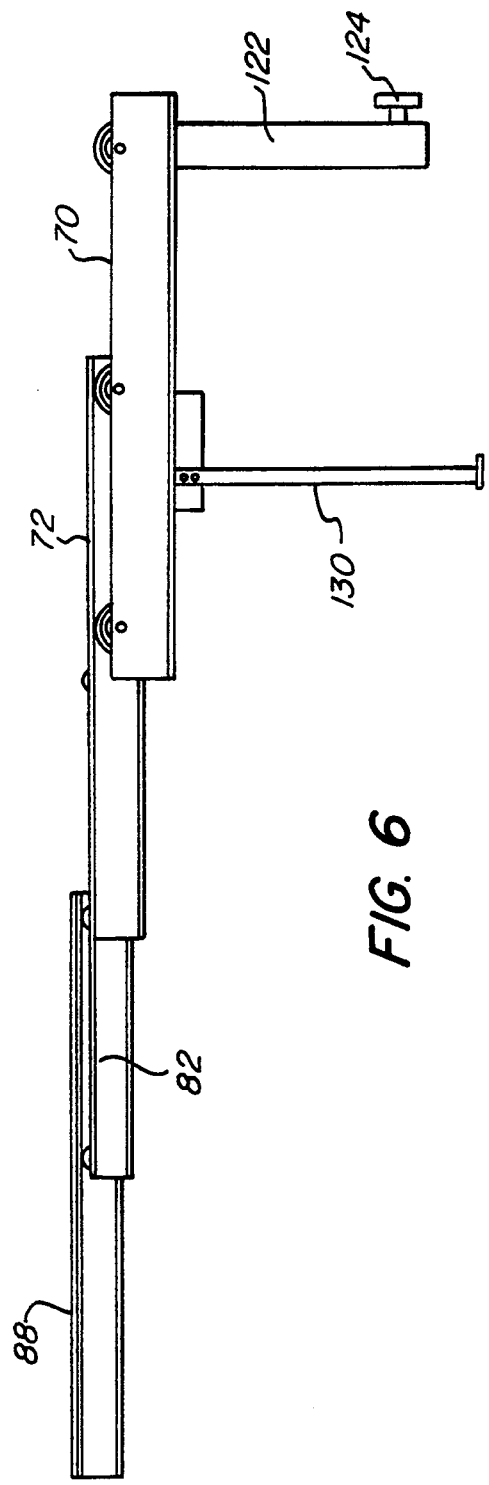
FIG. 6 is a side plan view of FIG. 5 illustrating only the plates in the fully extended position.

Turning to FIGS. 3 and 4, the robot assembly 14 includes a hydraulic cylinder 64 mounted on the base of the frame 22 which is controlled by the computer 20 to drive the robot assembly in the vertical direction. The hydraulic cylinder 64 includes a piston 66 which is coupled by a mounting block 68 to a stationary plate 70. An electronic weight sensing device 69 is seated between the mounting block 68 and the stationary plate 70, and is coupled to the computer 20 to transmit signals to the computer 20 indicative of the pressure exerted on the top of the robot assembly 14. The computer 20 is responsive to these signals to determine the weight of each load of medical waste transported by the robot assembly 14, as is described further below. The robot assembly 14 also includes an assembly of plates seated one on top of the other on the stationary plate 70, which are driven relative to each other in a telescopic fashion in the horizontal direction to transport the waste container 28 from the decontamination chamber 12 to the compactor 16.

A first plate 72 is mounted directly on top of the stationary plate 70, and includes a pair of U-shaped channel members 74 mounted on opposite sides of the first plate relative to each other. Each U-shaped channel member 74 receives three rollers 76 mounted on L-shaped supports 80, which are in turn mounted on opposite sides of the stationary plate 70 relative to each other. Thus, the stationary plate 70 includes six rollers 76, three rollers 76 mounted on each side of the plate and spaced apart from each other along the respective side of the plate, as shown in FIG. 3.

A second plate 82 is mounted on top of the first plate 80, and includes a pair of U-shaped channel members 84 mounted on opposite sides of the second plate relative to each other. Each U-shaped channel member 84 receives three rollers 86 mounted on the U-shaped channel members 74 of the first plate 72. Thus, the first plate 72 includes six rollers 86, three rollers 86 mounted on each side of the plate and spaced apart from each other along the respective side of the plate.

A third or top plate 88 is mounted directly above the second plate 82, and includes a pair of U-shaped channel members 90 mounted on the underside of the top plate. Each U-shaped channel member 90 receives a set of three rollers 92, each set of rollers 92 being mounted on a respective U-shaped channel member 84 of the second plate 82 and spaced apart from each other along the length of the channel member.

As shown in FIGS. 5 through 8, each plate is driven horizontally on the respective sets of rollers relative to the plate immediately beneath it. A bi-directional drive motor 94 is mounted beneath the stationary plate 70, and as shown in FIGS. 4 and 8, includes a chain 96 for driving the plates 72, 82, and 88 relative to each other in the horizontal direction. The drive motor 94 includes a drive sprocket 98 for driving the chain 96, and the ends of the chain 96 are each coupled to an opposite end of one of the U-shaped channel members 76 of the first plate 72, as shown in FIGS. 4 and 8. Three intermediate sprockets 100 are mounted on the adjacent L-shaped member 80 of the stationary plate 70, and are spaced apart from each other to guide the chain 96, as shown in FIG. 8.

As shown in FIG. 7, the plates of the robot assembly 14 are also coupled together by a pair of first cables 102 and a pair of second cables 104 to drive the plates in the horizontal direction in response to movement of the chain 96. There are two sets of cables 102 and 104, each set being located on one side of the plates to drive the plates in a respective horizontal direction in response to corresponding movement of the chain 96. The cables 102 and 104 on one side drive the plates in the direction of the compactor 16, as shown in FIG. 7, whereas the cables 102 and 104 on the other side of the plates drive the plates in the direction of the decontamination chamber 12. As shown in FIG. 7, the cables 102 and 104 on one side of the plates are arranged in the mirror image of the cables 102 and 104 on the other side of the plates.

As shown in FIG. 7, each first cable 102 is secured on one end to a respective side of the stationary plate 70, is wrapped around a respective pulley 106 on the opposite side of the first plate 72, and is secured on its other end to the same side of the second plate 82 as the side to which it is attached on the stationary plate 70. Each second cable 104 is similarly secured on one end to a respective side of the first plate 72, is wrapped around a respective pulley 108 mounted on the opposite side of the second plate 82, and is secured on the same side of the top plate 88 as the side of the second plate 106 to which it is attached.

Accordingly, when the motor 94 is driven in the direction indicated by the arrow in FIG. 8, the plates 72, 82 and 88 are driven in the horizontal direction (toward the compactor 16) as illustrated in FIG. 7. The chain 96 drives the second plate 72 to the left in FIG. 7, which in turn causes the first cable 102 to simultaneously drive the second plate 82 in the same direction, and causes the second cable 104 to simultaneously drive the top plate 88 in the same direction. The plates 72, 82, and 88 are then driven back into their horizontal-home position, as shown in FIG. 8, by driving the motor 94 in the opposite direction, which in turn causes the cables 102 and 104 on the opposite side of the plates to drive the second plate 82 and top plate 88 in the same direction with the first plate 72. Thus, depending on the direction in which the motor 94 is driven, the top plate 88 can be driven into the decontamination chamber 12 to pick-up the waste container 28, and then driven into the compactor 16 to release the decontaminated waste for compaction and disposal, as is described further below.

The robot assembly 14 also includes several guide blocks and corresponding guide members located between the plates to guide the plates in the horizontal direction and to substantially prevent lateral movement of the plates. As shown in FIG. 4, a first guide block 110 is mounted on one side of the stationary plate 70, and a corresponding first guide member 112 projects downward from the first plate 72 in sliding engagement with the first guide block 110. A second guide block 114 is mounted on the top surface of the first plate 72, on an opposite side of the plate relative to the first guide member 112, and a corresponding second guide member 116 projects downward from the second plate 82 in sliding engagement with the second guide block 114. A third guide block 118 is mounted on the top surface of the second plate 82, and defines a slot for receiving a corresponding third guide member 120 projecting downward from the underside of the top plate 88.

An anti-rotation arm 122 is supported from the end of the stationary plate 70 opposite the motor 94, and includes a guide roller 124 which is received within a corresponding U-shaped channel 126 mounted on the frame 22, as shown in FIG. 1B. As the stationary plate 70 is moved in the vertical direction by the cylinder 64, the roller 124 is driven and maintained within the U-shaped channel 126, and thus prevents any rotational movement of the robot assembly.

The robot assembly 14 further includes a position sensor 128 mounted on one side of the stationary plate 70, which is coupled to the computer 20 and transmits a signal when the top plate 88 is located in the horizontal-home position, as shown in FIG. 3. Several level sensors are also mounted on the hydraulic cylinder 64 and coupled to the computer to sense the level of the plate assembly. A sensor actuator 130 is suspended from the mounting block 68, and thus moves vertically with the plate assembly when the cylinder 64 is actuated. A first sensor 132 is mounted near the base of the cylinder 64, and transmits a signal to the computer 20 when aligned with the sensor actuator 130, thus indicating that the top plate 88 is in the vertical home position. A second sensor 134 is located above the first sensor 132, and transmits a signal to the computer 20 when aligned with the sensor actuator 130, indicating that the plates 72, 82 and 88 are in position to be driven horizontally into the decontamination chamber 12 or out of the compactor 16. A third sensor 136 is located above the second sensor 134, and similarly transmits a signal to the computer 20 when aligned with the sensor actuator 130, indicating that the top plate 88 has been driven upward a distance sufficient to lift the waste container 28 off of the loading tray 24 for transport into the compactor 16. The motor 94 also includes an optical encoder which transmits signals to the computer 20 indicative of the horizontal distance that the plates 72, 82, and 88 have been moved in order to control the horizontal movement of the robot assembly.

Turning to FIG. 1B, the compactor 16 includes a compactor ram 138 which is driven by a first hydraulic cylinder 140 and second hydraulic cylinder 142. The two hydraulic cylinders 140 and 142 are mounted in a staggered, parallel relationship relative to each other and are coupled to the computer 20 for controlling operation of the cylinders. The first cylinder 140 includes a first piston 141 coupled to the top wall of the compactor 16, and the second cylinder 142 includes a second piston 144 coupled to the compactor ram 138. Actuation of the first cylinder 140 causes the piston 141 to drive both the cylinder assembly 140 and 142, and the compactor ram 138 downward. Then, upon completion of the stroke of the first piston 141, actuation of the second cylinder 142 causes the second piston 144 to continue driving the compactor ram 138 downward to complete compaction of the decontaminated waste. A pressure switch 143 is coupled between the hydraulic cylinders 140 and 142 and the computer 20, and is adjusted to terminate operation of the cylinders when the hydraulic pressure reaches a threshold setting, typically within the range of approximately 1500 to 2500 psi.

As shown in FIGS. 1B, 9 and 10, the compactor ram 138 includes a compacting surface defining a plurality of raised surface areas 146 and contiguous depressed surface areas 148. In the embodiment of the present invention illustrated, the raised surface areas and contiguous depressed surface areas form a plurality of truncated pyramids. This uneven surface configuration facilitates in crushing and otherwise deforming and altering the appearance of the decontaminated waste upon compaction. The compactor ram 138 also has a bucket-type configuration, including four side walls 149 defining a hollow interior for receiving the cylinder assembly 140 and 142. The four side walls 149 of the compactor ram 138 are dimensioned to slide within side walls 151 of the compactor, as shown in FIG. 1B. One advantage of this generally rectangular, bucket-type configuration, is that the compactor ram 138 is maintained in a substantially level position as it is driven up and down within the side walls 151 of the compactor. As will be recognized by those skilled in the art, it may be desirable to periodically lubricate the side walls 151 of the compactor.

A pair of collapsible load trays 150 are mounted on either side of the compactor beneath the compactor ram 138. Each collapsible tray 150 is mounted by a spring-biased hinge 152 to the frame 22, which normally maintains the trays 150 in the horizontal position, as shown in dashed lines in FIG. 2. The distance between the two trays 150 is sufficient to permit the top plate 88 of the robot assembly 14 to move between the trays, yet is less than the width of the waste container 28 in order for the trays 150 to receive the waste container from the robot assembly, and support the waste container to permit the decontaminated waste to cool prior to compaction. Thus, the force applied by each spring-biased hinge 152 is selected so that it is sufficient to hold the waste container 28 on the loading trays 150 when the container is filled with decontaminated waste. However, once the decontaminated waste is cooled, the compactor ram 138 is driven downward against the waste container 28, so that the load trays 150 collapse downward against the sides of the compactor, and the decontaminated waste is crushed and compacted into a waste bin 154 located in the bottom of the compactor. The waste bin 154 is mounted on wheels, as shown in FIG. 1B, so that when filled it can be rolled out of the compactor 16 and emptied. The waste bin 154 is enclosed by an access door 155 with a solenoid-operated lock (not shown), in the same manner as with the door 32 for the decontamination chamber 12 to prevent access during operation and avoid the possibility of injury. The middle and top portions of the compactor 16 are similarly enclosed by access doors 155 with solenoid-operated locks (not shown) for gaining access to these portions of the apparatus 10 for maintenance and repair.

The compactor 16 also includes a first limit switch 155 mounted in the top of the compactor and coupled to the computer 20 to transmit a signal to the computer when the compactor ram 138 is located in the top or home position, as shown in FIG. 1B. A second limit switch 157 is mounted adjacent the loading trays 150, as also shown in FIG. 1B, and transmits a signal to the computer 20 each time the top of the adjacent wall 149 of the compactor ram 138 passes beneath the switch, and thus indicates a completion of the downward stroke of the compactor ram. When the bin 154 is full, the compactor ram 149 is unable to pass entirely beneath the second limit switch 157. The computer 20 is responsive to the absence of this signal, and generates an audible and/or visual signal to the operator indicating that the bin 154 is full. Another limit switch 159 is mounted in the base of the compactor 16 adjacent the rear of the bin 154, and transmits a signal to the computer 20 when the bin 154 is either absent or not properly seated within the compactor. The computer 20 is responsive to this signal to prevent operation of the compactor 16 until the bin 154 is properly seated within the compactor. The computer 20 is preferably programmed to drive the compactor ram 138 to crush the waste with multiple hits, i.e., several short downward strokes, once the compactor ram 138 reaches the end of its first downward stroke. For example, once the first downward stroke is completed as indicated by the pressure switch 143, the computer 20 responds by driving the compactor ram 138 through several shorter strokes (e.g., each stroke is below the collapsible trays 150) to facilitate complete compaction and physical alteration of the waste.

One advantage of the parallel-oriented hydraulic cylinders 140 and 142, is that they reduce the overall height of the apparatus 10, yet have a sufficient stroke to fully compact the decontaminated waste in the waste bin 154 located at the base of the apparatus. With prior single-cylinder configurations, the single cylinder would have to be longer in order to have a sufficient stroke to crush the waste, and thus the apparatus would have to be taller to house such a cylinder. In the apparatus of the present invention, on the other hand, because there are two cylinders oriented in a parallel relationship to each other, the overall height of the apparatus can be sufficiently low to fit through a standard door frame. This is a significant advantage in facilitating installation of the apparatus in a hospital or other facility.

The cool-air circulation system 18 includes a main duct 156 extending across the top of the apparatus 10 and along one side of the compactor 16, as shown in FIG. 1B. One end of the main duct 156 is coupled to an exhaust port 158 in the side of the compactor 16, and the other end of the main duct is coupled to an exhaust port 160 in the top of the apparatus 10. The exhaust port 160 is coupled to any suitable venting system in the facility for venting the filtered exhaust air into the atmosphere. A blower 162 is coupled to the main duct 156 immediately upstream of the exhaust port 158 for drawing the air through the system.

A filter assembly 164 is mounted in the main duct 156 immediately prior to the blower 162 for filtering the air prior to passage through the exhaust port 160. The filter assembly comprises several filters mounted in succession, including a pre-filter 166, a HEPA filter 168, and an activated carbon filter 170. The HEPA filter 168 is provided to remove any particulates and the carbon filter 170 is provided to substantially remove odors and gas. A pressure gauge 172 of a type known to those skilled in the art, such as a magnahelic gauge, is coupled to the computer 20 for monitoring the pressure drop across the filter assembly 164 to ensure that the filters are replaced when necessary. The pressure gauge 172 transmits a signal to the computer 20 when the pressure drop across the filter assembly reaches a threshold value. The computer 20 responds to the warning signal by initiating a time clock, and upon expiration of the predetermined time period, the computer generates a signal to replace the filters. As indicated by the dashed lines and arrows in FIG. 1B, the cool-air circulation system 18 causes the relatively cool air to flow through the space above the robot assembly 14 and through the compactor 16 to cool the decontaminated waste prior to compaction. The system 18 also filters the air through the filter assembly 164 so that it can be simply vented into the atmosphere. The filter assemblies and other components of both the cool-air and hot-air systems can be accessed through a door 173 located on the front of the apparatus, as shown in FIG. 1A.

The cool-air circulation system 18 also includes an air conditioning unit 174 mounted in the base of the apparatus beneath the decontamination chamber 12, as shown in FIG. 1B. A temperature sensor 176 is coupled to the computer 20 and mounted in the main duct 156 to monitor the temperature of the exhaust air. The computer 20 is responsive to the temperature sensor 176 to operate the air conditioning unit when the temperature of the exhaust air exceeds a threshold value. The air conditioning unit 174 blows refrigerated air into the space above the robot assembly 14, which is in turn drawn through the compactor 16 and into the main duct 156. The air conditioning unit 174 can be accessed through a door 175 located on the front of the apparatus, as shown in FIG. 1A. The mid-section of the apparatus 10, including the robot assembly 14, is similarly accessed through a door 177 on the front of the apparatus, as shown in FIG. 1A. The doors 175 and 177 may also include solenoid-operated door locks (not shown) for preventing access during the operation of the apparatus.

The apparatus 10 also includes a fire suppression system 178 mounted adjacent the decontamination chamber 12, as shown in FIG. 1A. The fire suppression system 178 includes a temperature sensor which activates the system if the temperature In the decontamination chamber reaches a predetermined combustion range. The fire suppression system 178 includes a canister with a supply of $CO_2$, or other known fire suppressant, for injection into the decontamination chamber 12 in the event of a fire by means of a pair of conduits 180 coupled between the decontamination chamber 12 and the $CO_2$ canister. The conduits 180 preferably include quick-disconnect fittings on the exterior of the apparatus 10 to permit rapid and easy replacement of the $CO_2$ canister. The computer 20 is also coupled to the fire suppression system 178, so that in the event of a fire, the computer 20 responds by shutting down the entire apparatus.

The apparatus 10 also includes a dyeing system 181 mounted above the passageway between the robot assembly 14 and the compactor 16, as shown in FIG. 1B. The dyeing system 181 contains a water-based dyeing solution, and comprises a pump (not shown) and nozzles 182 (only one shown) directed downward toward the waste container 28 as it is transported by the robot assembly 14 into the compactor 16, to spray the decontaminated waste with the dye solution, and thus give the outside surface of the waste a substantially uniform color and appearance. An optical sensor 184 is mounted adjacent the nozzles 182, and transmits a signal to the computer 20 in response to the passage of the waste container 28 beneath the sensor. The computer 20 is responsive to the signal from the sensor 184 to actuate the pump of the dyeing system 181, and in turn spray the waste with the dye solution. One advantage of this feature is that it gives the decontaminated waste a substantially uniform and innocuous appearance by dyeing the outside surface of the decontaminated waste the color grey, for example.

In the operation of the apparatus of the present invention, when the system is turned on, the computer 20 automatically runs through a self-test cycle, during which each of the components is briefly operated to be sure that everything is functioning as required. At the end of the self-test cycle, the computer 20 enters a preheat mode, in which it activates the heating panel 40 in the decontamination chamber 12 to bring the system up to operating temperature. Once the system is normalized at the operating temperature (as indicated by the thermocouple 54), the computer 20 generates an audible signal and/or a visual prompt on the control panel 21 to inform the operator that the apparatus is ready to accept a load of infectious or contaminated waste for treatment.

The operator then opens the access door 32 and places the waste container 28 filled with contaminated waste onto the loading tray 24. The operator then closes the door 32, which in turn automatically places the waste container 28 in position for decontamination within the decontamination chamber, and for automatic removal by the robot assembly 14 once the decontamination cycle is completed.

The decontamination cycle is initiated by depressing a "cycle start" button on the operator panel coupled to the computer 20, which automatically actuates the door lock 39 on the access door 32 to prevent access to the decontamination chamber. Based upon the volume of waste and the operating temperature of the decontamination chamber 12, the computer 20 automatically runs the decontamination cycle for a predetermined period of time. In the embodiment of the present invention illustrated, the decontamination cycle is within the range of approximately 15 to 45 minutes. Upon expiration of the decontamination cycle, the decontaminated waste is automatically retrieved, cooled, and compacted, as hereinafter described.

At the end of the decontamination cycle, the computer 20 actuates the drive motor 56 to open the rear doors 58 to the decontamination chamber 12. When the doors 58 are fully opened, the second position switch 62 is actuated, and the computer 20 responds by actuating the cylinder 64 of the robot assembly 14 to move the piston 66 up. When the cylinder 64 reaches the first vertical position, the second sensor 134 transmits a signal to the computer 20, indicating that the plates 72, 82, and 88 are appropriately positioned for horizontal movement. The computer 20 responds to the signal from the second sensor 134 by stopping the cylinder 64, and actuating the drive motor 94 to drive the plate assembly into the decontamination chamber 12. The optical encoder on the motor 94 transmits signals indicative of the horizontal distance travelled by the plates 72, 82 and 88, and the computer 20 is programmed to stop the motor 94 when the top plate 88 is located beneath the waste container 28, as shown in dashed lines in FIG. 1B.

The top plate 88 is dimensioned to fit between the two loading arms 26 of the loading tray 24. Thus, once the top plate 88 reaches its end position in the decontamination chamber 12, the computer 20 stops the motor 94, and actuates the cylinder 64 to drive the top plate 88 upward and lift the waste container 28 above the loading tray 24. The third sensor 136 transmits a signal to the computer 20 when the waste container 28 is lifted above the loading tray 24, and is in position for removal from the decontamination chamber 12. The computer 20 responds to the third sensor 136 by stopping the cylinder 64, and actuating the drive motor 94 in the opposite direction to remove the waste container 28 from the decontamination chamber 12, and into a position in the compactor 16 immediately above the collapsible load trays 150. As the waste container 28 passes beneath the dyeing system 180, the computer 20 responds to the signal from the sensor 184 by controlling the dyeing system to spray the dye solution onto the decontaminated waste.

Once the top plate 88 reaches its end position in the compactor 16, as indicated by the optical encoder on the drive motor 94, the computer stops the drive motor 94, and actuates the cylinder 64 to move the plate assembly from level two (position sensor 136) down to level one (position sensor 134). The top plate 88 is then lowered between the collapsible trays 150, and in turn causes the waste container 28 to rest in a cooling position on the collapsible trays 150. The computer 20 then actuates the drive motor 94 to drive the plate assembly back to its horizontal-home position, as shown in FIGS. 3 and 4. Once the top plate 88 is in the horizontal-home position, as indicated by the position sensor 128, the drive motor 94 is stopped, and the cylinder 64 is actuated to return the robot assembly 14 to its vertical-home position, as indicated by the first sensor 132.

The computer 20 then actuates the drive motor 56 to close the rear doors 58 on the decontamination chamber 12. Once the doors 58 are fully closed, as indicated by the first position switch 60, another load of waste can be deposited in the decontamination chamber 12 and the decontamination cycle repeated. Upon expiration of a predetermined cooling period (which expires prior to expiration of the next decontamination cycle), the computer 20 successively actuates the cylinders 140 and 142 in the compactor 16 to drive the compactor ram 138 downward and into the decontaminated waste. The waste container 28 is in turn driven through the collapsible loading trays 150 (which fold down against the adjacent walls of the compactor 16) and into the loading bin 154. As described above, the unique surface configuration of the compactor ram 138 crushes the waste and alters its appearance so that it is generally unrecognizable. The computer 20 is preferably programmed to control the second cylinder 142 to drive the second piston 144 through several short strokes upon completing its first downward stroke to ensure thorough compaction of the waste.

The decontamination, cooling, and compacting cycles are automatically repeated for each load of waste. The waste bin 154 is filled when the top of the wall 149 of the compactor ram 138 is unable to pass beneath the second limit switch 157 (i.e., the compacted waste prevents the piston 144 from driving through its full stroke because of the pressure limit set by pressure switch 143). The computer 20 responds to this condition by generating an audible signal so that the operator can empty the waste bin 154.

As will be recognized by those skilled in the art, the computer 20 can be programmed to shut down at a designated time following decontamination of the last load of waste. The shut down is done on a sequential basis, so that the heating panel 40 is turned off prior to turning off the air circulation and cooling systems. Likewise, the computer 20 can be programmed to automatically start the system each day, and to run the system through the self-test cycle prior to receiving the first load of waste.

At the end of each process cycle (i.e., after decontamination and compaction of a load of waste), the computer 20 generates a hard copy of activity by means of a printer 186 mounted within the control panel 21 indicating the length of time of the process cycle, the operating temperature of the decontamination chamber, the time of day, the load process number, and the weight of the load. Of course, other pertinent data can equally be obtained and recorded as it is desired in a manner known to those of ordinary skill in the art.

I claim:

1. An apparatus for disposing of waste, comprising:
   a decontamination chamber adapted to receive waste and for decontaminating said waste therein:
   compacting means for reducing the volume of the waste subsequent to decontamination wherein said compacting means comprises a pair of collapsible loading trays for supporting the waste prior to compaction and a waste bin in the bottom of the compactor, said loading trays adapted to collapse against the compactor walls upon compaction enabling the waste to be crushed and compacted into said waste bin; and
   robot assembling means communicating between the decontamination chamber and said compactor means for automatically retrieving the waste from the decontamination chamber upon being decontaminated and transporting the waste to the compactor means for volume reduction prior to disposal, said robot assembling means comprising at least one plate and means for driving said plate in a first direction from a home position into the decontamination chamber to retrieve waste and in a second direction from the home position, into the compactor to deliver the waste, the second direction differs from said first direction.

2. An apparatus as defined in claim 1 wherein the decontamination chamber, compacting means and robot assembling means are contained within a common housing structure having front, top, bottom and back walls joined by opposed side walls.

3. An apparatus as defined in claim 2, wherein the decontamination chamber comprises an access door in the front wall of the housing for accessing the interior of the decontamination chamber, and a loading tray for holding the waste during decontamination, said loading tray including a pair of loading arms spaced apart from each other on either side of said tray, said tray adapted to support a waste container, the loading tray being mounted to said chamber to pivot within the decontamination chamber and communicating with the access door for movement with the access door, whereby upon opening the door, the loading tray is pivoted through the access door into a load position to receive and hold the waste container and, upon closing the door, the loading tray is pivoted into the decontamination chamber, said loading arms being generally parallel to the access door.

4. An apparatus as defined in claim 3, further comprising means for automatically locking the access door during decontamination to prevent access to the decontamination chamber during decontamination.

5. An apparatus as defined in claim 2, wherein the compacting means comprises a compactor ram, a first drive cylinder containing a first piston hydraulically operable therein coupled to the top wall of the housing, and a second drive cylinder containing a second piston hydraulically operable therein coupled to the compactor ram, the first and second drive cylinders being in a substantially parallel relationship relative to each other to drive the compactor ram.

6. An apparatus as defined in claim 1, additionally comprising at least one infrared heating panel within the decontamination chamber for thermally decontaminating the waste.

7. The apparatus as defined in claim 6 wherein the decontamination chamber additionally comprises exhaust means to permit vapors formed upon heating to bleed from the decontamination chamber.

8. An apparatus as defined in claim 1, further comprising a hot-air circulation system communicating with the decontamination chamber for circulating air through the decontamination chamber and to facilitate heating of the waste by convection.

9. An apparatus as defined in claim 8, wherein the hot-air circulation system comprises means for filtering the air within the decontamination chamber.

10. An apparatus as defined in claim 1, further comprising a cool-air circulation system for circulating air adjacent the robot assembling means and through the compacting means for cooling the decontaminated waste prior to compaction.

11. An apparatus as defined in claim 10, wherein the cool-air circulation system includes at least one first filter for filtering particulates from the air prior to venting the air from the apparatus.

12. An apparatus as defined in claim 11, wherein the cool-air circulation system additionally comprises at least one second filter for filtering at least one of gases and odors from the air prior to venting the air from the apparatus.

13. An apparatus as defined in claim 1, wherein the robot assembly comprises a plate assembly comprising at least two plates, one mounted on top of the other, and means for driving at least one plate relative to the other to transport the waste between the decontamination chamber and the compacting means.

14. An apparatus as defined in claim 13, wherein the robot assembly further comprises means for driving at least one plate in the vertical direction for lifting the waste in the decontamination chamber and lowering the waste in the compacting means.

15. An apparatus as defined in claim 14, wherein the means for driving the at least one plate in the vertical direction comprises a cylinder coupled to the plate assembly.

16. An apparatus as defined in claim 1, wherein the compacting means comprises a compactor ram for compacting the waste, the compactor ram defining a plurality of raised surface areas and a plurality of contiguous depressed surface areas surrounding the raised surface areas for facilitating compaction and altering the appearance of the waste upon being compacted.

17. An apparatus as defined in claim 1, wherein the decontamination chamber comprises means for heating the waste by radiation and means for heating the waste by convection.

18. An apparatus as defined in claim 1, further comprising a cardboard container for holding the waste during decontamination in the decontamination chamber and for compaction with the waste in the compacting means.

19. An apparatus as defined in claim 1, further comprising means for dyeing the waste subsequent to decontamination.

20. An apparatus as defined in claim 1, wherein the robot assembling means includes means for determining the weight of each load of decontaminated waste transported by the robot assembly.

21. An apparatus for disposing of waste as defined in claim 1, wherein the compacting means comprises:
a housing having a top wall;
a compactor ram located within said housing;
a first drive cylinder containing a first piston hydraulically operable therein coupled to the top wall of the housing; and
a second drive cylinder including a second piston hydraulically operable therein coupled to the compactor ram at one end, and to the first piston at a second end which is opposed to the first end, said first and second drive cylinders being oriented in a substantially parallel relationship relative to each other to drive the compactor ram.

22. An apparatus for disposing of waste as defined in claim 21, wherein the compactor ram of the compacting means defines a plurality of raised surface areas and a plurality of contiguous depressed surface areas surrounding the raised surface areas for facilitating compaction and altering the appearance of the waste upon being compacted.

23. An apparatus for disposing of waste as defined in claim 22, wherein the raised surface areas and contiguous depressed surface areas of the compactor ram define a plurality of truncated pyramids.

24. An apparatus for disposing of waste, comprising:
a decontamination chamber adapted to receive waste and for decontaminating said waste therein;
compacting means for reducing the volume of the waste subsequent to decontamination; and
robot assembling means communicating between the decontamination chamber and said compactor means for automatically retrieving the waste from the decontamination chamber upon being decontaminated and transporting the waste to the compactor means for volume reduction prior to disposal, said robot assembly means comprising at least one plate and means for driving said plate into the decontamination chamber to retrieve waste and into the compactor to deliver the waste, wherein the decontaminating chamber, the compacting means, and the robot assembling means are contained within a common housing structure having front, top and back walls joined by opposed side walls, further wherein the decontaminating chamber comprises an access door in the front wall of the housing for accessing the interior of the decontaminating chamber, and a loading tray including a pair of loading arms spaced apart from each other on either side of said tray, said tray adapted to support a waste container, the loading tray being mounted to said chamber to pivot within the decontamination chamber and communicating with the access door for movement with the access door, whereby upon opening the door, the loading tray is pivoted through the access door into a load position to receive and hold the waste container and, upon closing the door, the loading tray is pivoted into the decontamination chamber, said loading arms being generally parallel to the access door.

25. An apparatus as defined in claim 24, further comprising means for automatically locking the access door during decontamination to prevent access to the decontamination chamber during decontamination.

26. An apparatus for disposing of waste, comprising:
a decontamination chamber adapted to receive waste and for decontaminating said waste therein;
compacting means for reducing the volume of the waste subsequent to decontamination, said compacting means comprises a pair of collapsible loading trays for supporting the waste prior to compaction and a waste bin in the bottom of the compactor, said loading trays adapted to collapse against the compactor walls upon compaction enabling the waste to be crushed and compacted into said waste bin; and
robot assembling means communicating between the decontamination chamber and said compactor means for automatically retrieving the waste from the decontamination chamber upon being decontaminated and transporting the waste to the compactor means for volume reduction prior to disposal, said robot assembly means comprising at least one plate and means for driving said plate into the decontamination chamber to retrieve waste and into the compactor to deliver the waste.

* * * * *